US011732232B2

(12) United States Patent
Jung et al.

(10) Patent No.: US 11,732,232 B2
(45) Date of Patent: Aug. 22, 2023

(54) BIOMIMETIC CELL CULTURE APPARATUS AND CELL CULTURE SYSTEM COMPRISING THE SAME

(71) Applicant: KOREA RESEARCH INSTITUTE OF BIOSCIENCE AND BIOTECHNOLOGY, Daejeon (KR)

(72) Inventors: Cho Rok Jung, Daejeon (KR); Jung Hwa Lim, Daejeon (KR); Hyun Mi Kang, Daejeon (KR); Kyung Hee Noh, Daejeon (KR); Kyung Sook Chung, Daejeon (KR); Mi Young Son, Daejeon (KR); Myung Jin Son, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 475 days.

(21) Appl. No.: 16/993,314

(22) Filed: Aug. 14, 2020

(65) Prior Publication Data

US 2022/0049205 A1 Feb. 17, 2022

(51) Int. Cl.
*C12M 1/36* (2006.01)
*C12M 1/42* (2006.01)
*C12M 3/00* (2006.01)
*C12M 1/34* (2006.01)

(52) U.S. Cl.
CPC ............ *C12M 41/48* (2013.01); *C12M 21/08* (2013.01); *C12M 35/04* (2013.01); *C12M 41/40* (2013.01)

(58) Field of Classification Search
CPC ...... C12M 41/48; C12M 41/40; C12M 21/08; C12M 35/04; C12M 35/08; C12M 23/58; C12M 25/04; C12M 27/16; C12M 29/00
See application file for complete search history.

(56) References Cited

U.S. PATENT DOCUMENTS

| 2,701,229 A | 2/1955 | Scherr |
| 4,201,845 A | 5/1980 | Feder et al. |
| 5,358,871 A | 10/1994 | Stevens et al. |
| 5,366,893 A | 11/1994 | Stevens et al. |
| 5,527,705 A | 6/1996 | Mussi et al. |

(Continued)

FOREIGN PATENT DOCUMENTS

| CN | 1460122 A | 12/2003 |
| CN | 1875093 A | 12/2006 |

(Continued)

OTHER PUBLICATIONS

Machine Translation of WO_2013183121_A1_H (Year: 2023).*

(Continued)

*Primary Examiner* — Michael L Hobbs
(74) *Attorney, Agent, or Firm* — Harness, Dickey & Pierce, P.L.C.

(57) ABSTRACT

The present disclosure provides a biomimetic cell culture apparatus that mimics interactions among organs in a human body. The present disclosure includes a plurality of culture units for culturing cells, a conduit for connecting the plurality of culture units to each other to form a circulating path, a pump unit disposed on the conduit for forming a flow in culture medium such that the culture medium circulates through the plurality of culture units, and an agitating module for agitating the plurality of culture units.

14 Claims, 17 Drawing Sheets

(56) References Cited

U.S. PATENT DOCUMENTS

| | | | |
|---|---|---|---|
| 5,612,188 | A | 3/1997 | Shuler et al. |
| 5,766,937 | A | 6/1998 | Lahm et al. |
| 6,066,496 | A | 5/2000 | Bridges |
| 6,329,195 | B1 | 12/2001 | Pfaller |
| 7,186,548 | B2 | 3/2007 | Li |
| 7,524,315 | B2 | 4/2009 | Blott et al. |
| 7,727,759 | B2 | 6/2010 | Ozawa et al. |
| 9,057,715 | B2 | 6/2015 | Kim et al. |
| 10,041,032 | B2 | 8/2018 | Lee |
| 2004/0132175 | A1 | 7/2004 | Vetillard et al. |
| 2005/0101010 | A1 | 5/2005 | Li |
| 2005/0158701 | A1 | 7/2005 | West |
| 2005/0244957 | A1 | 11/2005 | Stock |
| 2006/0051857 | A1 | 3/2006 | Wedell et al. |
| 2007/0161106 | A1 | 7/2007 | Jervis et al. |
| 2007/0172814 | A1 | 7/2007 | Li |
| 2007/0172944 | A1 | 7/2007 | Li |
| 2007/0178441 | A1 | 8/2007 | Li |
| 2008/0076170 | A1 | 3/2008 | Annala et al. |
| 2009/0035856 | A1* | 2/2009 | Galliher ............... C12M 29/10 435/294.1 |
| 2009/0037031 | A1 | 2/2009 | George et al. |
| 2009/0246872 | A1 | 10/2009 | Ozawa et al. |
| 2010/0099172 | A1 | 4/2010 | West |
| 2010/0107752 | A1 | 5/2010 | Fernando |
| 2010/0203638 | A1 | 8/2010 | Adachi et al. |
| 2010/0261226 | A1 | 10/2010 | Niazi |
| 2010/0304472 | A1 | 12/2010 | Kim et al. |
| 2012/0065782 | A1 | 3/2012 | West |
| 2013/0143230 | A1 | 6/2013 | Tolias et al. |
| 2013/0245830 | A1 | 9/2013 | West |
| 2015/0010990 | A1 | 1/2015 | West |
| 2015/0072401 | A1* | 3/2015 | Nozaki ............... C12M 37/00 435/303.1 |
| 2015/0191687 | A1 | 7/2015 | Jung et al. |
| 2016/0108351 | A1 | 4/2016 | Lee |
| 2016/0348059 | A1 | 12/2016 | West |
| 2020/0224147 | A1* | 7/2020 | Rogers ............... C12M 21/08 |

FOREIGN PATENT DOCUMENTS

| | | |
|---|---|---|
| CN | 201729833 U | 2/2011 |
| CN | 202181306 U | 4/2012 |
| CN | 103555577 A | 2/2014 |
| DE | 1017751 B | 10/1957 |
| EP | 0790300 A2 | 8/1997 |
| EP | 2832847 A1 | 2/2015 |
| JP | H06327462 A | 11/1994 |
| JP | 2005095015 A | 4/2005 |
| JP | 2007312730 A | 12/2007 |
| JP | 2009502183 A | 1/2009 |
| JP | 2009118820 A | 6/2009 |
| JP | 2010168122 A | 8/2010 |
| JP | 2011504748 A | 2/2011 |
| JP | 5197753 B2 | 5/2013 |
| KR | 20010029122 A | 4/2001 |
| KR | 20060007978 A | 1/2006 |
| KR | 100679248 B1 | 2/2007 |
| KR | 20070087076 A | 8/2007 |
| KR | 20090065643 A | 6/2009 |
| KR | 20090126930 A | 12/2009 |
| KR | 20110133382 A | 12/2011 |
| KR | 101235378 B1 | 2/2013 |
| KR | 20130100643 A | 9/2013 |
| KR | 101341572 B1 | 12/2013 |
| KR | 101362293 B1 | 2/2014 |
| KR | 101393108 B1 | 5/2014 |
| KR | 101412155 B1 | 6/2014 |
| KR | 101422345 B1 | 7/2014 |
| KR | 20140091270 A | 7/2014 |
| KR | 20150044708 A | 4/2015 |
| KR | 20150054377 A | 5/2015 |
| KR | 101566083 B1 | 11/2015 |
| KR | 101610646 B1 | 4/2016 |
| KR | 101743231 B1 | 6/2017 |
| KR | 20180000487 U | 2/2018 |
| KR | 101864410 B1 | 6/2018 |
| WO | WO-94/28501 A1 | 12/1994 |
| WO | WO-2009/069962 A2 | 6/2009 |
| WO | WO-2009/078637 A2 | 6/2009 |
| WO | WO-2013183121 A1 * | 12/2013 ............ C12M 25/04 |
| WO | WO-2014062022 A1 | 4/2014 |
| WO | WO-2017047986 A1 | 3/2017 |

OTHER PUBLICATIONS

"Development of in vivo mimic circulating culture system for alternative experiment" Dec. 30, 2014, pp. 1-42.

So-youn Kim et al., "Development of culture system for biomimicked bioreactor" Last Accessed on Aug. 12, 2020, pp. 3743-3746.

Dong Hyeok Park "Development of a 3D Perfusion Cell Culture System Mimicking in vivo Microenvironment" Pusan National University, Oct. 6, 2016, pp. 1-51.

Ho et al.,"Mini-chamber system for longterm maintenance and observation of cultured cells" (Year 2005).

Liu, Pinghuai, "Biotechnology experiments", Mar. 2012, Nanjing university Press, pp. 172-173.

Wang, Binghe et al.., "Drug Delivery Principles and Applications", Jan. 31, 2008, p. 76.

Zhang Juntian, "Modern Pharmacological Experimental Methods" Jul. 1, 2012, China Peking Union Medical College, pp. 1533-1536.

Liu, Pinghuai, "Biotechnology experiments", Mar. 2012, Nanjing university Press, pp. 172-173. English translation provided.

Wang, Binghe et al.., "Drug Delivery Principles and Applications", Jan. 31, 2008, p. 76. English translation provided.

Zhang Juntian, "Modern Pharmacological Experimental Methods" Jul. 1, 2012, China Peking Union Medical College, pp. 1533-1536. English translation provided.

Chinese Office Action dated Jun. 12, 2016 issued in corresponding Chinese Patent Application No. 201380032703.6. English translation provided.

Yonghyun Gwon, et al. "Engineering Biomimetic Platforms of in vivo-line Microenvironments for Modeling of Cellular Functions," Trans. Korean Soc. Mech. Eng. B. vol. 43, No. 12, pp. 847-857.

Database WPI week 200163 Thomson Scientific, London, GB; AN 2001-563609 XP002755235.

Database WPI Week 201128 Thomson Scientific, London, GB; AN 2011-D55246 XP002755236.

* cited by examiner

BIOMIMETIC CELL CULTURE APPARATUS
AND CELL CULTURE SYSTEM
COMPRISING THE SAME

TECHNICAL FIELD

The present disclosure relates to a cell culture apparatus and a cell culture system that culture cells based on interactions of the different cells, and more particularly, to a cell culture apparatus and a cell culture system that culture cells by in vivo mimicking.

BACKGROUND

Cell culture is a very important technology in biological research, including molecular biology, and refers to culturing a specific cell for a purpose of developing technology for diagnostics and therapeutics of human disease. In general, the cell culture is achieved using cell culture container and apparatus. A conventional cell culture tool includes a plastic flask, a culture dish, and the like, and the cell culture apparatus includes an incubator, a bio-reactor, or the like.

In the conventional cell culture, cell culture preparation is completed by putting cells of a single type or at least one type into one closed culture container, adding suitable culture medium for each cell, and putting the culture container into the cell culture apparatus.

The cell culture apparatus proliferates the cells by creating a specific environment suitable for a purpose of the cell culture. When the cell proliferation is complete, the cells are recovered and observed through a microscope or used for tests of various purposes.

Mostly, the conventional cell culture apparatus is conducted for a single cell culture, thereby has a limit in culturing cells of various types and measuring various effects resulted from interactions therebetween.

To solve such problem, recently, an organ-chip cell culture tool that attaches the cells of the various types to the cell culture tool in a chip form in which small chambers are connected to each other to observe the interactions between the cells has been developed.

However, because of a relatively small scale, the organ-chip has a limit in that it is difficult to provide an environment suitable for culturing a cell structure composed of a sufficient number of or a large number of cells, and sample securing for analysis of a result after the cell culture is also insufficient.

On the other hands, in drug development field, before a human clinical trial, pharmacokinetics, pharmacodynamics, clinical effects, and adverse reactions of the corresponding drug in animals are evaluated for a purpose of proving efficacy and safety of the drug generally.

This is referred to as a non-clinical trial. In the non-clinical trial, generally, after drug administration to rodents (a mouse, a rat, and the like), a change in a concentration of the drug in blood and a reactivity (an efficacy, a toxicity, and the like) to the drug are observed. The change in the concentration of the drug in the body is determined by absorption, distribution, metabolism, and excretion (ADME).

More specifically, when the drug is administered to the body, first, the drug is introduced into plasma from an administration site, and second, the drug introduced into the plasma is distributed into stroma or a cell. Third, the drug is metabolized by a liver, a kidney, or a tissue. Finally, the drug and a metabolite thereof are excreted in urine, sweat, or the like. Such series of processes is referred to as the ADME, the absorption, the distribution, the metabolism, and the excretion of the drug.

In one example, because a result of the non-clinical trial conducted on the animal does not reflect a reaction of a human body, there is a case in which a drug that has passed the animal trial shows the unexpected toxicity or does not exhibit the efficacy in the clinical trial conducted on the humans. Such problem leads to a failure of the new drug development and is pointed out as a cause of huge cost consumption and risk.

To solve such problem, a research for developing a biomimetic cell culture apparatus capable of testing the ADME using a cell culture apparatus that mimics an interaction between a human cell and a human organ has been conducted.

SUMMARY

The present disclosure has been made to solve the above-mentioned problems occurring in the prior art while advantages achieved by the prior art are maintained intact.

An aspect of the present disclosure provides a biomimetic cell culture apparatus that mimics an interaction of human organs to connect a plurality of cells to each other to interact with each other, and provides an optimal cell culture environment in which each cell representing each organ is able to function. In addition, a pharmacokinetics (PK/PD) test similar to a result of a human body may be performed using the present disclosure. However, such task is exemplary, and the scope of the present disclosure is not limited thereto.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, a cell culture apparatus includes a plurality of culture units for culturing cells, a conduit for connecting the plurality of culture units to each other to form a circulating path, a pump unit disposed on the conduit for forming a flow in culture medium such that the culture medium circulates through the plurality of culture units, and an agitating module for agitating the plurality of culture units.

In one implementation, the agitating module may move or shake the plurality of culture units in at least one direction.

In one implementation, the cell culture apparatus may further include a stage having one surface for mounting the plurality of culture units thereon and the other surface connected to the agitating module.

In one implementation, the culture unit may include a main body connected to the conduit, a holder disposed in an inner space of the main body and having a plurality of insertion openings defined therein, and an insert to be respectively inserted into at least one of the insertion openings and supported by the holder, wherein the cells are arranged in the insert.

In one implementation, the holder may further include at least one side opening defined in a side wall thereof to face the conduit.

In one implementation, the holder may further include a guide opening connected to one side of each of the insertion openings.

In one implementation, the insert may include a fluid passing portion disposed on at least one of a bottom and a side wall of the insert, and the culture medium may pass through the fluid passing portion.

In one implementation, the fluid passing portion may be formed of a mesh shape.

In one implementation, a number of the inserts to be placed in each culture unit may be set based on a relative ratio of each cell to be cultured in each culture unit.

In one implementation, the cell culture apparatus may further include a load cell unit disposed below the culture unit to measure an amount of culture medium introduced into the culture unit.

In one implementation, the cell culture apparatus may further include a controller that drives the pump unit to adjust the culture medium stored in each culture unit based on weight data of each culture unit measured by the load cell unit.

In one implementation, the cell culture apparatus may further include a sub-unit connected to a circulation circuit connected to the conduit, and the sub-unit may supply or extract fluid to or from the conduit.

According to an aspect of the present disclosure, a cell culture apparatus may include a main body having a connecting end and storing culture medium therein, wherein the culture medium is introduced into the connecting end, a holder disposed in an inner space of the main body and having a plurality of insertion openings, and an insert to be respectively inserted into at least one of the insertion openings and supported by the holder, wherein cells are arranged in the insert.

In one implementation, the holder may further include at least one side opening defined in a side wall thereof to face the connecting end.

In one implementation, the holder may further include a guide opening connected to one side of each of the insertion openings.

In one implementation, the insert may include a fluid passing portion disposed on at least one of a bottom and a side wall of the insert, wherein the culture medium may pass through the fluid passing portion.

According to an aspect of the present disclosure, a cell culture system may include a plurality of cell culture apparatuses interconnected with each other so that culture medium may circulate, wherein each of the plurality of cell culture apparatuses may include a main body having a connecting end and storing the culture medium therein, wherein the culture medium is introduced into the connecting end, a holder disposed in an inner space of the main body and having a plurality of insertion openings, and an insert to be respectively inserted into at least one of the insertion openings and supported by the holder, wherein cells are arranged in the insert, and wherein a number of the inserts to be placed in each cell culture apparatus may be set based on a relative ratio of each cell to be cultured.

Other aspects, features, and advantages other than those described above will become apparent from the following detailed description, claims, and drawings for implementing the invention below.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
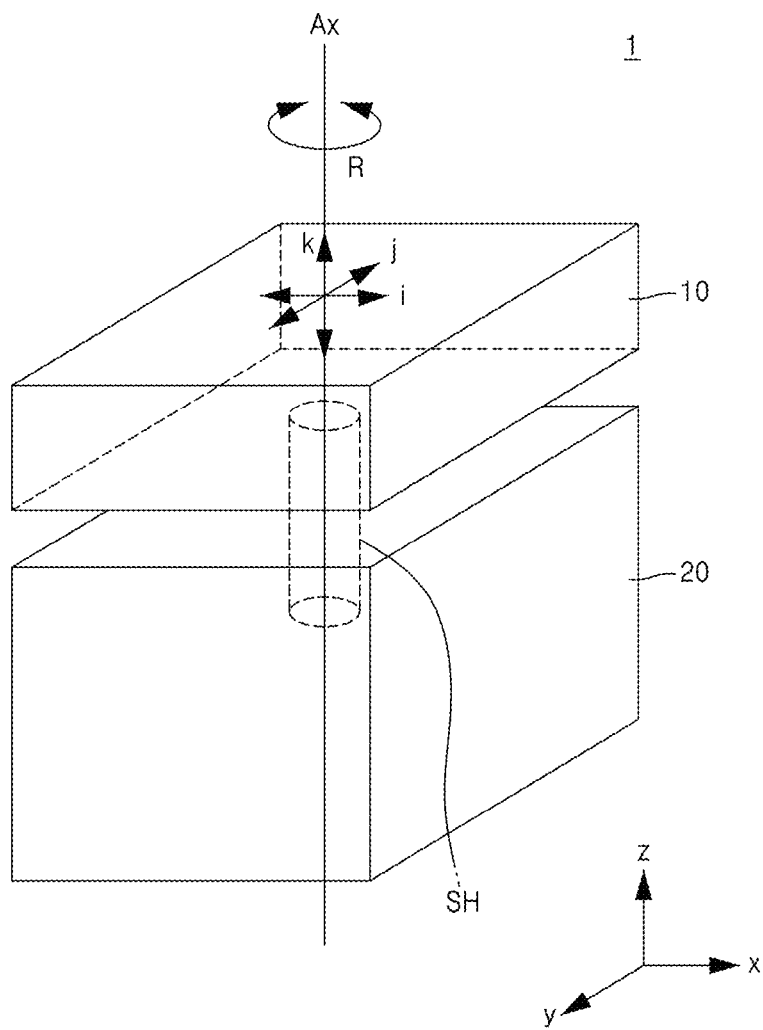
FIG. 1 is a perspective view schematically showing a cell culture apparatus according to an embodiment of the present disclosure.

Hereinafter, various embodiments of the present disclosure are described in connection with the accompanying drawings. Various embodiments of the present disclosure may have various modifications and various embodiments, so that specific embodiments are illustrated in the drawings and detailed descriptions related thereto are described. However, it should be understood that this is not intended to limit the various embodiments of the present disclosure to specific embodiments, and include all modifications and/or equivalents or substitutes included in the spirit and technical scope of the various embodiments of the present disclosure. In connection with the description of the drawings, similar reference numerals have been used for similar components.

Expressions such as "include" or "may include" that may be used in various embodiments of the present disclosure indicate the presence of a corresponding function, an operation, a component, or the like that is disclosed, and do not limit additional at least one function, operation, component, or the like. It should be understood that the terms "comprises", "comprising", "includes", and "including" in various embodiments of the present disclosure, specify the presence of the features, numbers, steps, operations, components, parts, or combinations thereof, but do not preclude the presence or addition of one or more other features, numbers, steps, operations, components, parts, or combinations thereof.

In various embodiments of the present disclosure, expressions such as "or" include any and all combinations of words listed together. For example, "A or B" may include A, may include B, or may include both A and B.

Expressions such as "first" or "second" used in various embodiments of the present disclosure may modify various components in various embodiments, but do not limit the corresponding components. For example, the above expressions do not limit the order and/or importance of the corresponding components. The above expressions may be used to distinguish one component from another component.

For example, the first user device and the second user device are both user devices and represent different user devices. For example, a first component may be referred to as a second component, and similarly, a second component may be referred to as a first component without departing from the scope of rights of various embodiments of the present disclosure.

It should be understood that if it is described in the specification that one component is "connected," "coupled" or "joined" to another component, a third component may be "connected," "coupled," and "joined" between the first and second components, although the first component may be directly connected, coupled or joined to the second component. On the other hand, it should be understood that if it is described in the specification that one component is "directly connected", "directly coupled" or "directly joined" to another component, the third component does not exist between the first and second components.

Terms used in various embodiments of the present disclosure are only used to describe a specific embodiment, and are not intended to limit the various embodiments of the present disclosure. The singular forms "a" and "an" are intended to include the plural forms as well, unless the context clearly indicates otherwise.

Unless otherwise defined, all terms including technical and scientific terms used herein have the same meaning as commonly understood by one of ordinary skill in the art to which this disclosure belongs.

Terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a perspective view schematically showing a cell culture apparatus 1 according to an embodiment of the present disclosure.

Referring to FIG. 1, the cell culture apparatus 1 includes a culture module 10 and an agitating module 20. The agitating module 20 may agitate the culture module 10, and a cell may be cultured in the culture module 10.

The cell culture apparatus 1 is an apparatus for culturing the cell with culture medium. The cultured cell may not be limited to a specific type, and may be variously applied depending on a purpose of the culture. For example, the cell may be a cell of an animal, a plant, or a human.

The culture module 10 is connected to the agitating module 20 through a connecting shaft SH. The agitating module 20 may be driven to agitate the culture module 10. When the culture module 10 is moved or vibrated by the agitation, the culture of the cell disposed inside the culture module 10 may be stimulated.

The agitating module 20 may move the culture module 10 in at least one direction or vibrate the culture module 10. For example, the culture module 10 may be moved in at least one of an i direction, a j direction, and a k direction by the driving of the agitating module 20. In addition, the culture module 10 may be rotated in an R direction by the driving of the agitating module 20.

Figure 2:
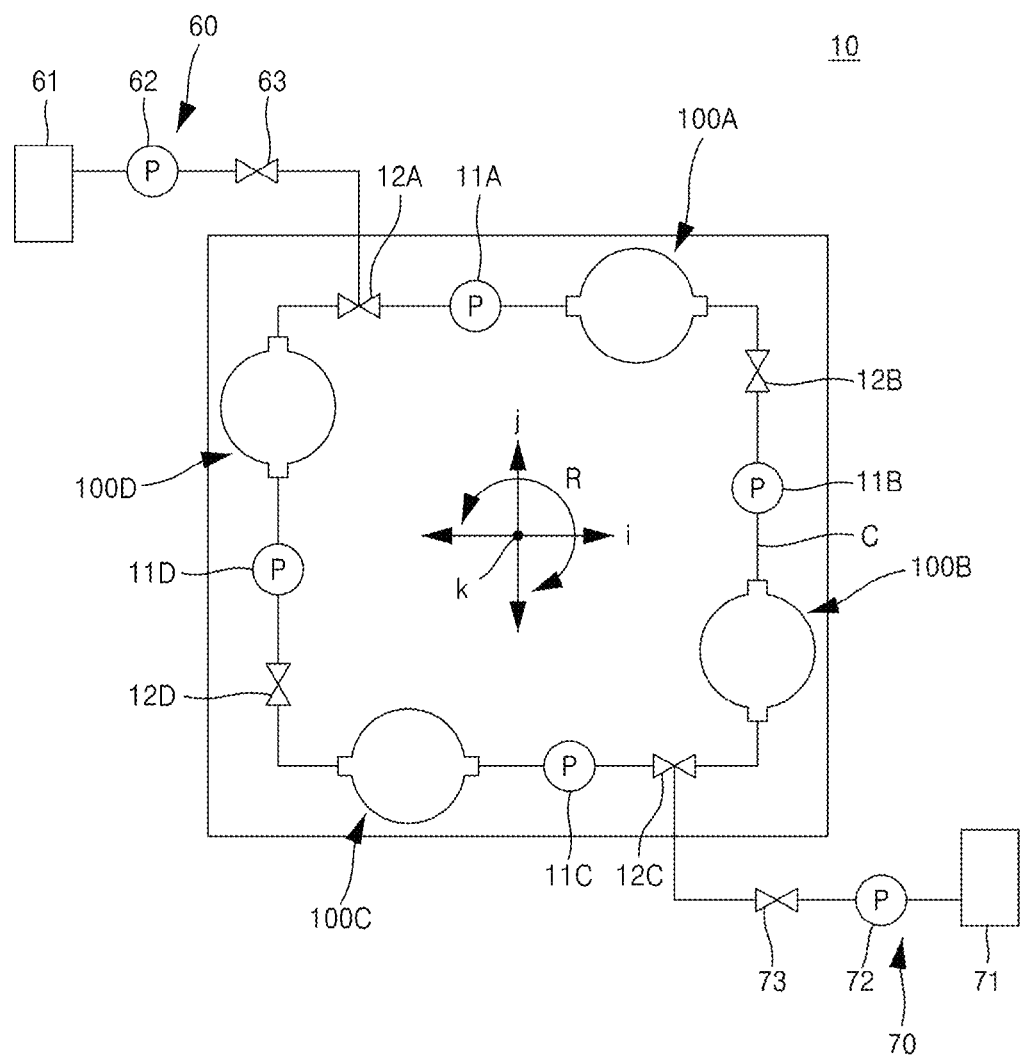
FIG. 2 is a view showing a culture module according to an embodiment of the present disclosure.

FIG. 2 is a view showing the culture module 10 according to an embodiment of the present disclosure.

Referring to FIGS. 1 and 2, the culture module 10 is disposed on a stage 10A, and includes a plurality of culture units 100. The plurality of culture units 100 may be connected to each other by a conduit C to implement a circulation circuit.

A pump unit 11 and a valve unit 12 may be arranged on one side of the culture unit 100 to adjust a flow rate or a flow velocity of the culture medium introduced into and/or discharged from each culture unit 100.

The pump unit 11 includes a plurality of pumps. Each pump may be set as various types of pumps that may be applied to a fluid apparatus that cultures a cell. Each pump of the pump unit 11 may be controlled by a controller 50.

The valve unit 12 includes a plurality of valves. Each valve may be set as various types of valves that may be mounted on the conduit C to adjust a flow of the culture medium, add the culture medium, or extract the culture medium. An opening degree of each valve of the valve unit 12 may be adjusted by a user or by the controller 50.

The culture unit 100 may provide a space in which the cell is cultured, and the culture medium may be introduced into and discharged from the culture unit 100. The plurality of culture units 100 may be arranged along the conduit C. The number of culture units 100 may not be limited to a specific number, and may be variously set depending on the purpose of the culture. Hereinafter, for convenience of description, description will be made focusing on an embodiment in which four culture units are arranged on the stage 10A.

A first culture unit 100A, a second culture unit 100B, a third culture unit 100C, and a fourth culture unit 100D may be connected to the conduit C to form a circulation circuit.

The first culture unit 100A may adjust a flow rate and a flow velocity of culture medium flowed by a first pump 11A and a first valve 12A. The second culture unit 100B may adjust a flow rate and a flow velocity of culture medium flowed by a second pump 11B and a second valve 12B. The third culture unit 100C may adjust a flow rate and a flow velocity of culture medium flowed by a third pump 11C and a third valve 12C. The fourth culture unit 100D may adjust a flow rate and a flow velocity of culture medium flowed by a fourth pump 11D and a fourth valve 12D.

The stage 10A is connected to the agitating module 20, and the stage 10A is moved or vibrated in at least one direction of the i direction, the j direction, and the k direction by the driving of the agitating module 20, so that the first to the fourth culture units 100A to 100D arranged on the stage 10A may be agitated. In another embodiment, the first to the fourth culture units 100A to 100D may be agitated as the stage 10A rotates in the R direction.

As an optional embodiment, at least one sub-unit may be disposed on one side of the culture module 10. The sub-unit may be connected to the conduit C and connected to the circulation circuit, and may supply fluid to the conduit C or extract the fluid from the conduit C.

Specifically, a first sub-unit 60 may be disposed on one side of the culture module 10. The first sub-unit 60 may include a first reservoir 61, a first sub-pump 62, and a first sub-valve 63, and may supply fluid stored in the first reservoir 61 to the circulating conduit C.

When the first sub-pump 62 is driven and the first sub-valve 63 is opened, the fluid stored in the first reservoir 61 may be introduced into to the culture module 10 through the first valve 12A. Depending on a type of the culture medium stored in the first reservoir 61, the culture module 10 may set various environments to proceed with the culture of each cell.

For example, when the culture medium stored in the first reservoir 61 is the same as the culture medium circulating the culture unit 100, the first sub-unit 60 may additionally supply the culture medium to the culture module 10.

In another example, when the culture medium stored in the first reservoir 61 is different from the culture medium circulating the culture unit 100, the first sub-unit 60 may supply new culture medium to the culture module 10, and may change a culture condition depending on a cell culture step.

A second sub-unit 70 may be disposed on one side of the culture module 10. The second sub-unit 70 may include a second reservoir 71, a second sub-pump 72, and a second sub-valve 73, and the second sub-unit 70 may extract circulating culture medium.

When the second sub-pump 72 is driven and the second sub-valve 73 is opened, the culture medium flowing along the conduit C may be introduced into the second sub-unit 70 through the third valve 12C. The extracted culture medium may be stored in the second reservoir 71, and the culture medium may be inspected.

In addition, the second sub-unit 70 may also supply culture medium as the first sub-unit 60. That is, the plurality of sub-units may supply various culture media by supplying different culture media to the culture module 10.

Figure 3:
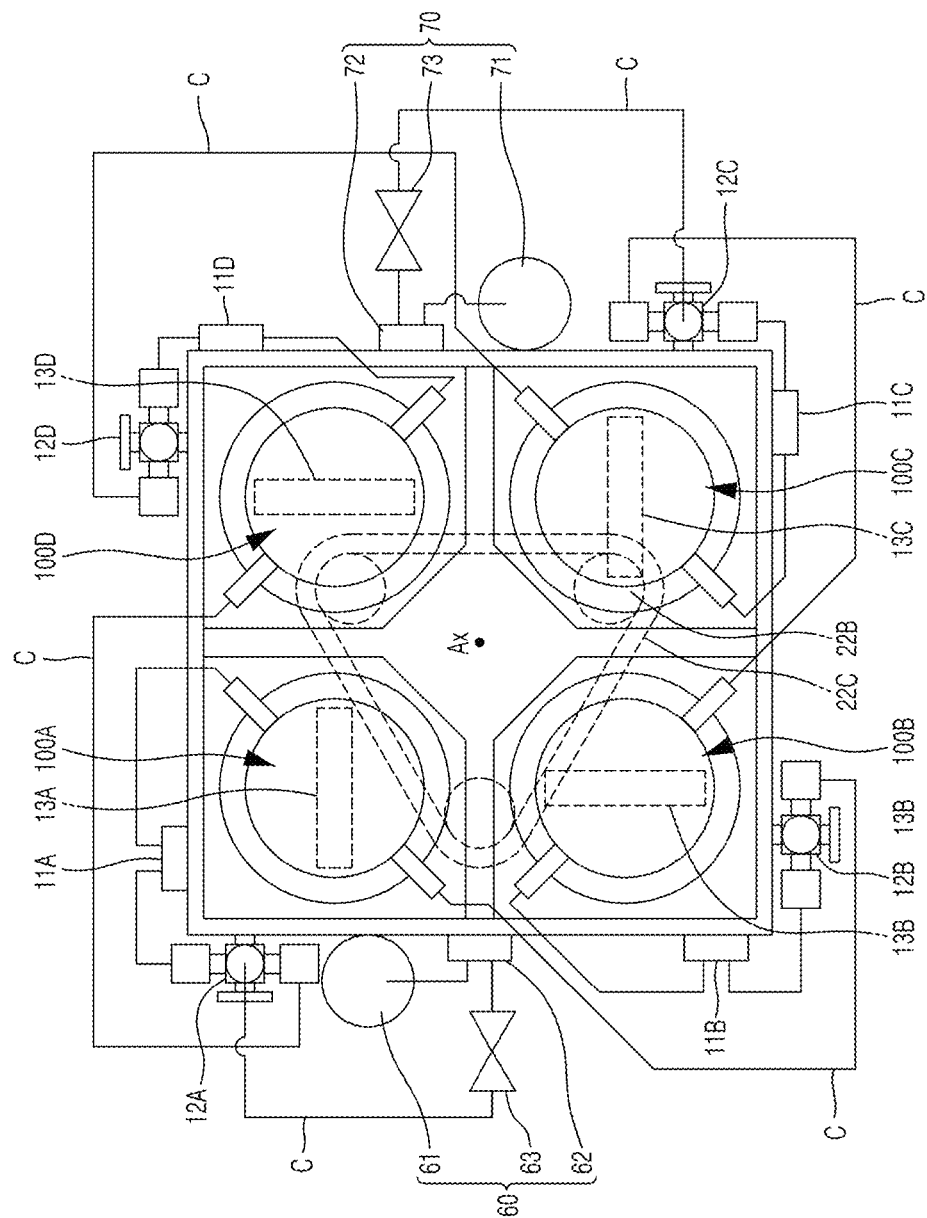
FIG. 3 is a plan view showing a cell culture apparatus according to an embodiment of the present disclosure.
Figure 4:
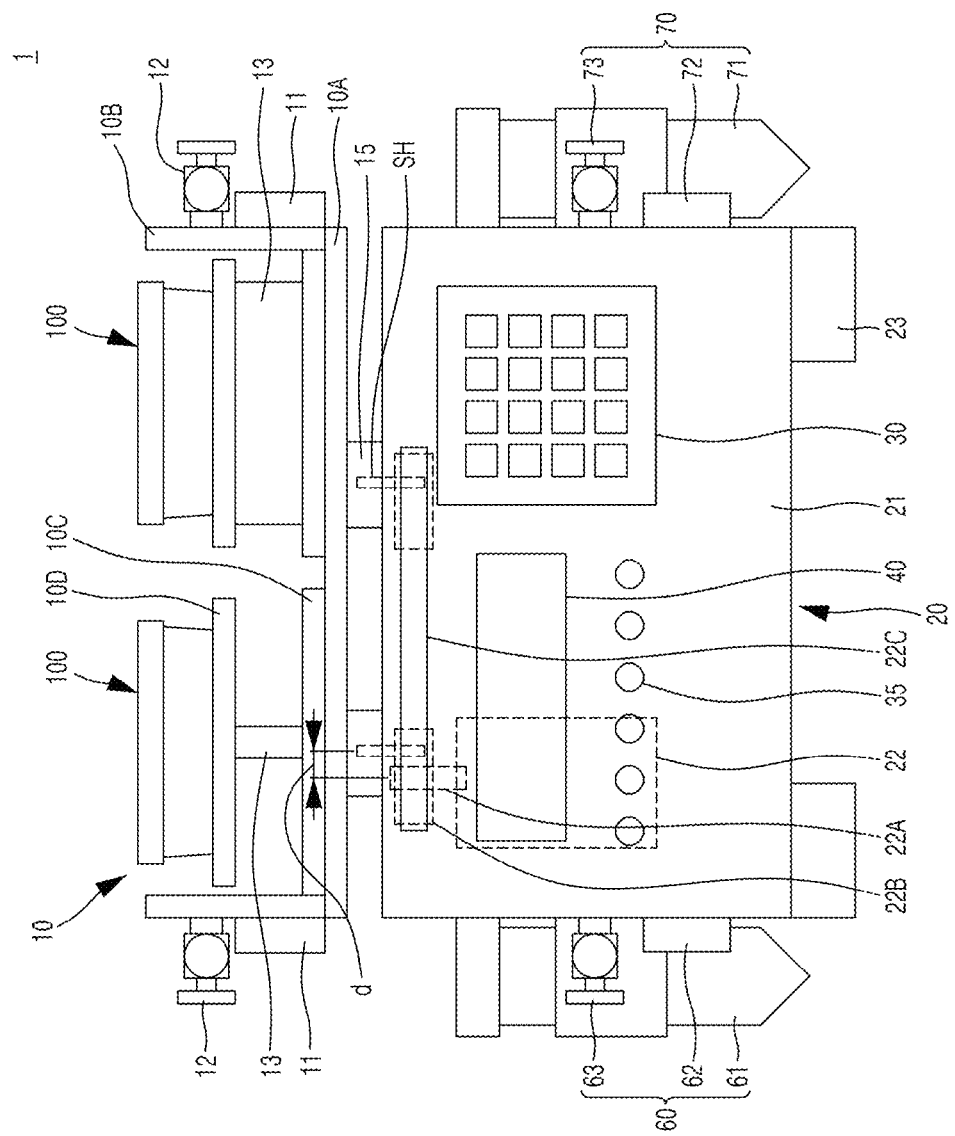
FIG. 4 is a front view showing a cell culture apparatus in FIG. 3.
Figure 5:
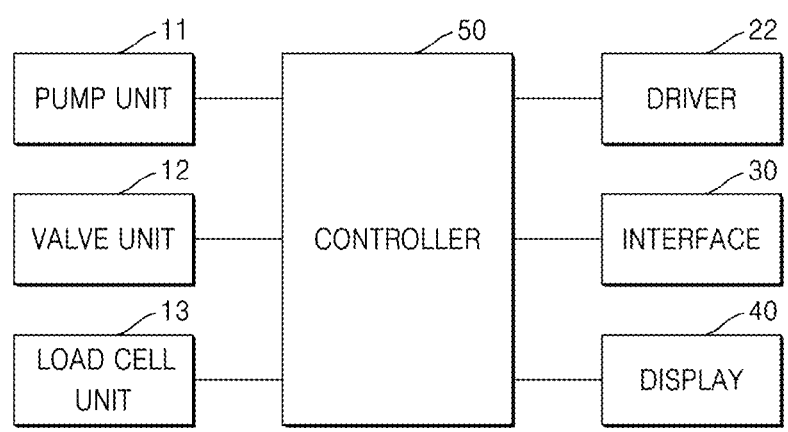
FIG. 5 is a block diagram showing a portion of a cell culture apparatus in FIG. 3.

FIG. 3 is a plan view showing the cell culture apparatus 1 according to an embodiment of the present disclosure, FIG. 4 is a front view showing the cell culture apparatus 1 in FIG. 3, and FIG. 5 is a block diagram showing a portion of the cell culture apparatus 1 in FIG. 3.

Referring to FIGS. 2 to 5, the cell culture apparatus 1 includes the culture module 10 and the agitating module 20. The culture units 100 of the culture module 10 may be agitated by the driving of the agitating module 20. The agitating module 20 may move or vibrate the plurality of culture units 100 in the at least one direction.

The culture module 10 has an inner space defined by the stage 10A and an outer wall 10B, and the plurality of culture units 100 are arranged in the inner space. The plurality of culture units 100 are arranged to circulate with each other. A culture effect resulted from an interaction of the cultured cells may be measured. That is, the culture module 10 may culture the cell by mimicking a body. This will be described in detail below.

The plurality of culture units 100 may be mounted on one surface of the stage 10A and the agitating module 20 may be connected to the other surface of the stage 10A. A first support plate 10C includes a plurality of first support plates in a number corresponding to the number of the culture units 100, and the first support plate 10C is disposed on the stage 10A. A second support plate 10D is disposed above the first support plate 10C, and the culture unit 100 is disposed above the second support plate 10D.

The outer wall 10B extends along an edge of the stage 10A. The pump unit 11 and the valve unit 12 may be fixed to the outer wall 10B.

The pump unit 11 may include at least one pump. In an embodiment, the pump unit 11 may include a plurality of pumps in a number corresponding to the number of culture units 100. When the first to the fourth culture units 100A to 100D are arranged as shown in FIG. 3, the pump unit 11 may include first to fourth pumps 11A to 11D.

The valve unit 12 may include at least one valve. In an embodiment, the valve unit 12 may include a plurality of valves in a number corresponding to the number of culture units 100 or pumps. When the first to the fourth culture units 100A to 100D are arranged as shown in FIG. 3, the valve unit 12 may include first to fourth valves 12A to 12D.

A load cell unit 13 may measure a weight of the culture unit 100. The load cell unit 13 may be disposed below the culture unit 100 and measure an amount of the culture medium introduced into the culture unit 100 or stored in the culture unit 100.

The load cell unit 13 may include a plurality of load cells in a number corresponding to the number of culture units 100. For example, a first load cell 13A is disposed below the first culture unit 100A, a second load cell 13B is disposed below the second culture unit 100B, a third load cell 13C may be disposed below the third culture unit 100C, and a fourth load cell 13D may be disposed below the fourth culture unit 100D.

The load cell unit 13 may be disposed between the first support plate 10C and the second support plate 10D to measure the weight of each culture unit 100, and the controller 50 may calculate the amount of the culture medium stored in the culture unit 100 based on the measured data.

A first connecting member 15 may be disposed beneath the stage 10A, and be connected to the agitating module 20. The first connecting member 15 and a second connecting member 22B of the agitating module 20 are connected to each other in a driving manner, so that the stage 10A may move and/or vibrate by driving of the second connecting member 22B.

In an embodiment, as shown in FIG. 3, a plurality of first connecting members 15 may be arranged beneath the stage, and each first connecting member 15 may be connected to each second connecting member 22B by each connecting shaft SH. The connecting shaft SH may have one end disposed at a center of the first connecting member 15, but may be eccentrically disposed by a distance d from a rotation axis of the second connecting member 22B. As a result, the stage 10A may vibrate by rotation of the second connecting member 22B, whereby the culture unit 100 may be agitated. Because of driving of a driver 22, the agitating module 20 may promote the cell culture while repeatedly moving in the i direction and the j direction.

The conduit C connects the first to the fourth culture units 100A to 100D to each other to circulate, thereby forming a passage through which the culture medium flows. In addition, the conduit C may connect the pump unit 11 and the valve unit 12 with each other.

The agitating module 20 may be disposed below the stage 10A, and may include a main housing 21 and the driver 22. In addition, a support block 23 that absorbs shock and supports the cell culture apparatus 1 may be disposed beneath the main housing 21.

The main housing 21 may form an exterior of the agitating module 20 to house the driver 22 and other electrical parts. In addition, the driving of the agitating module 20 may be controlled by the controller 50 which is installed inside the main housing 21.

The driver 22 may not be limited to a specific form, and various mechanical apparatuses that generate a driving force to agitate the culture unit 100 and deliver the driving force to the culture module 10 may be applied as the driver 22. The driver 22 may be disposed as an electric motor in an embodiment.

The driver 22 includes a driving shaft 22A. The second connecting member 22B may be disposed at an end of the driving shaft 22A. The plurality of second connecting members 22B may be arranged, and the driving force may be shared by a third connecting member 22C. That is, when one of the second connecting members 22B attached to the end of the driving shaft 22A rotates, the third connecting member 22C is driven, so that another second connecting member 22B may rotate. In this connection, the first connecting member 15 eccentrically connected to the second connecting member 22B is also driven, so that the culture module 10 may be agitated.

In an embodiment, the cell culture apparatus 1 may be agitated by an eccentric axis as described above. In another embodiment, although not shown in the drawing, as the stage of the cell culture apparatus 1 is rotated by the driving force of the driver 22, the culture unit 100 may be agitated. In addition, in the cell culture apparatus 1, the culture unit 100 may be agitated while the stage ascends and descends by the driving force of the driver 22.

The drawing shows that the culture units 100 are agitated together by the movement of the stage 10A, but the present disclosure is not limited thereto. Further, in the cell culture apparatus according to another embodiment, each culture unit 100 may be independently agitated. For example, the first to the fourth culture units 100A to 100D may be independently connected to the driver, and the first to the fourth culture units 100A to 100D may independently move or vibrate in the i direction, the j direction, and the k direction and rotate in the R direction to be agitated independently.

In the cell culture apparatus 1 according to the present disclosure, the plurality of culture units 100 are arranged on one plane. That is, the plurality of culture units 100 are arranged to form a monolayer. By the horizontally arranged culture units 100, the cells cultured in the culture units 100 may be easily observed during a test. In addition, the user may easily mount and separate the culture unit 100. In addition, because the plurality of culture units 100 are arranged on the same plane, when the culture test is stopped, the culture medium is not concentrated at one side, so that the test may be performed stably. On the other hand, when the culture units 100 are arranged in multiple layers, the culture medium flows to a lower layer when the test is stopped, so that each layer may not be able to have the same culture state.

The user may control driving of the cell culture apparatus 1 through an interface 30. By manipulating the interface 30, a driving time and a driving speed of the driver 22 may be controlled, each pump of the pump unit 11 may be controlled, and also the opening degree of each valve of the valve unit 12 may be controlled.

The interface 30 may be installed on one side of the main housing 21, and may be formed of a button, a touch screen, a knob, and the like. In addition, a plurality of buttons 35 are arranged on the main housing 21, so that the user may control the agitating module 20.

A display 40 may be installed on one side of the main housing 21 to display a state of the cell culture apparatus 1. The display 40 may display various information such as a driving state of the agitating module 20, a culture state of the culture module 10, and the like.

The display 40 may be implemented as display panels of various shapes. For example, the display panel may be implemented using various display technologies such as a liquid crystal display (LCD), an organic light emitting diode (OLED), an active-matrix organic light-emitting diode (AM-OLED), a liquid crystal on silicon (LcoS), a digital light processing (DLP), or the like. In addition, the display 40 may be coupled to at least one of a front surface region, a side surface region, and a rear face region of the display panel in a form of a flexible display.

The controller 50 may be connected to the culture module 10, the agitating module 20, the interface 30, and the display 40 to control an operation of the cell culture apparatus 1. The controller 50 may be connected to the pump unit 11, the valve unit 12, and the load cell unit 13, and may be connected to the driver 22.

The controller 50 may be connected to the pump unit 11 and the valve unit 12 to control the flow rate and flow velocity of the culture medium flowing to each culture unit 100. In particular, the controller 50 may adjust the culture medium stored in the culture unit 100 by controlling the pump and valve of each culture unit 100 based on the weight data measured by the load cell unit 13.

Specifically, the first to the fourth load cells 13A to 13D respectively measure weights of the first to the fourth culture units 100A to 100D. The controller 50 may calculate the amount of culture medium stored in the first to the fourth culture units 100A to 100D based on the measured data. The controller 50 may control driving of the first to the fourth pumps 11A to 11D or control the opening degrees of the first to the fourth valves 12A to 12D based on the calculated data to adjust a distribution of the culture medium.

For example, the controller 50 may flow the culture medium such that all of the first to fourth culture units 100A to 100D have the same weight.

In the cell culture apparatus 1, because the culture unit 100 has a balanced weight distribution, stability may be secured during the agitation. Because each culture unit 100 has substantially the same weight, the agitating module 20 is driven to stably drive the apparatus even when each culture unit 100 vibrates or reciprocates. Especially, even when the agitating module 20 drives the culture module 10 with high RPM or high frequency, the culture medium stored in each culture unit 100 does not overflow and the cell culture apparatus 1 does not fall, so that the stability may be secured.

In an embodiment, the controller 50 includes a processor (not shown), and specifically, the processor controls overall operations of the cell culture apparatus 1 using various stored programs. For example, the processor may include a CPU, a RAM, and/or a ROM. In this connection, the ROM stores a set of instructions for booting a system. In addition, the CPU copies an operating system stored in a memory of the cell culture apparatus 1 to the RAM in response to the instruction stored in the ROM, and executes the O/S to boot the system. When the booting is completed, the CPU may perform various operations by copying various applications stored in storage to the RAM and executing the various applications. In implementation, the controller 50 may be implemented as a plurality of CPUs (or DSPs, SoCs, and the like).

According to an embodiment of the present disclosure, the processor may be implemented as a digital signal processor (DSP) that processes a digital signal, a microprocessor, and a time controller (TCON). However, the processor may not be limited thereto, and may include at least one of a central processing unit (CPU), a micro controller unit (MCU), a micro processing unit (MPU), a controller, an application processor (AP), a communication processor (CP), and an ARM processor, or may be defined by the corresponding term. In addition, the processor may be implemented as a system on chip (SoC) and a large scale integration (LSI) with a built-in processing algorithm, or may be implemented in a form of a field programmable gate array (FPGA).

The cell culture apparatus 1 may include storage for storing a program for processing or controlling the processor and/or various data for an operation of the program. The storage may store a number of application programs (or applications) running on the cell culture apparatus 1, and data and instructions for the operation of the cell culture apparatus 1. At least some of such application programs may be downloaded from an external server and/or a cloud via wireless communication. In addition, at least some of such application programs may be stored in the cell culture apparatus 1 from a time of shipment for a basic function of the cell culture apparatus 1. The application program may be stored in a storage medium and driven by the processor to perform an operation (or a function) of the cell culture apparatus 1. In addition, the storage may include a DB that stores data for various cell culture conditions or cell culture methods. The cell culture conditions or the cell culture methods to be stored in the DB may be input by the interface 30, but may not be limited thereto, and may be transmitted through the external server or the cloud and/or an external terminal (not shown).

To this end, the controller 50 may further include a communication device (not shown) to transmit and receive the data. The communication device may include a short range communication device such as a Bluetooth communication device, a Bluetooth low energy (BLE) communication device, a near field communication device, a Wi-Fi (WLAN) communication device, a Zigbee communication device, an infrared data association (IrDA) communication device, a Wi-Fi Direct (WFD) communication device, a ultra wideband (UWB) communication device, an Ant+ communication device, and the like, and a mobile communication network.

In an embodiment, the cell culture apparatus 1 may be controlled through the external terminal (not shown). The terminal may receive a signal through the communication device of the cell culture apparatus 1. The user manipulates the terminal to perform the agitation function of the cell culture apparatus 1, and particularly, to control an agitation speed, a rotation speed, an agitation cycle, and the like. In addition, the user may adjust the driving of each pump by manipulating the terminal to adjust the flow of the culture medium toward the culture unit.

Each of the first sub-unit 60 and the second sub-unit 70 may be disposed on one side of the culture module 10 or the agitating module 20 to add the culture medium or extract the culture medium. The first sub-unit 60 may include the first reservoir 61, the first sub-pump 62, and the first sub-valve 63, and the second sub-unit 70 may include the second reservoir 71, the second sub-pump 72, and the second sub-valve 73.

In the cell culture apparatus 1 according to an embodiment of the present disclosure, because each culture unit is agitated, a culture efficiency may be increased. When the agitating module 20 moves or vibrates the culture module 10, the cell or the culture medium disposed inside each culture unit 100 are agitated. The cell culture apparatus 1 may increase an activity between the cell and the culture medium, thereby increasing the culture efficiency.

Figure 6:
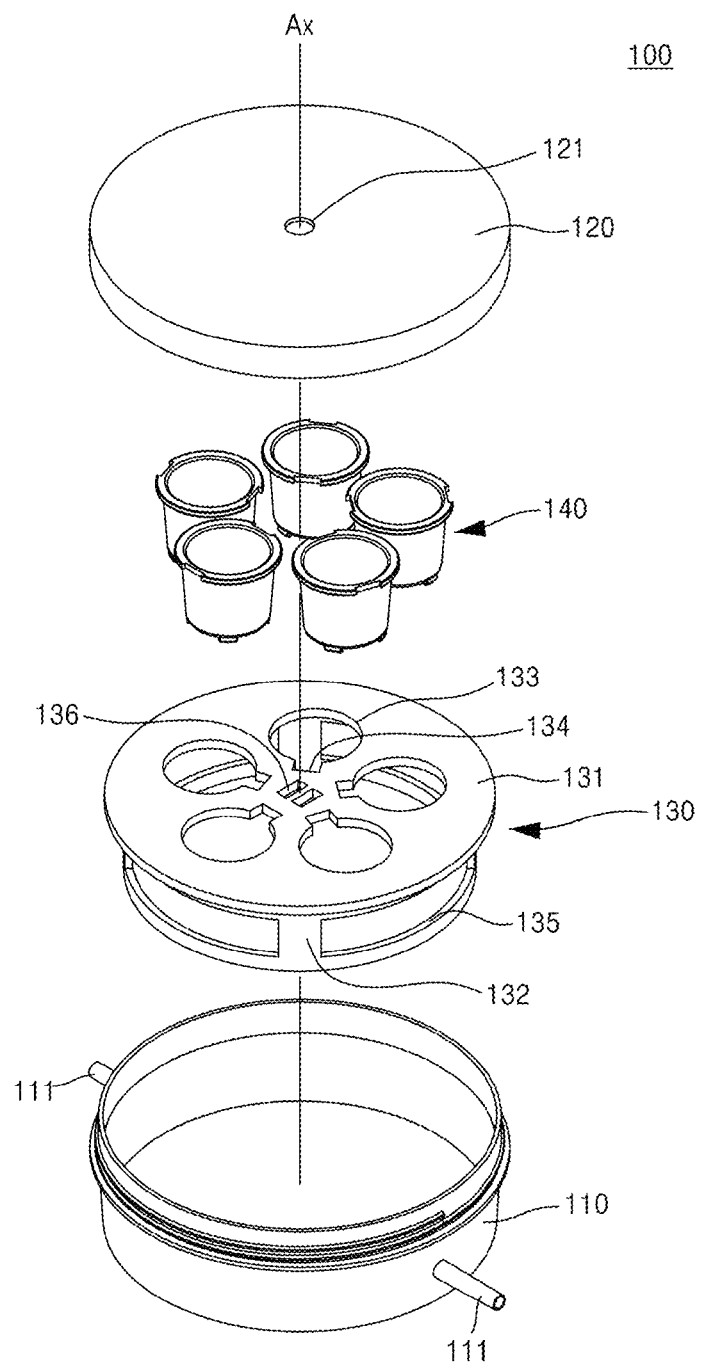
FIG. 6 is an exploded perspective view showing a culture unit according to an embodiment of the present disclosure.
Figure 7:
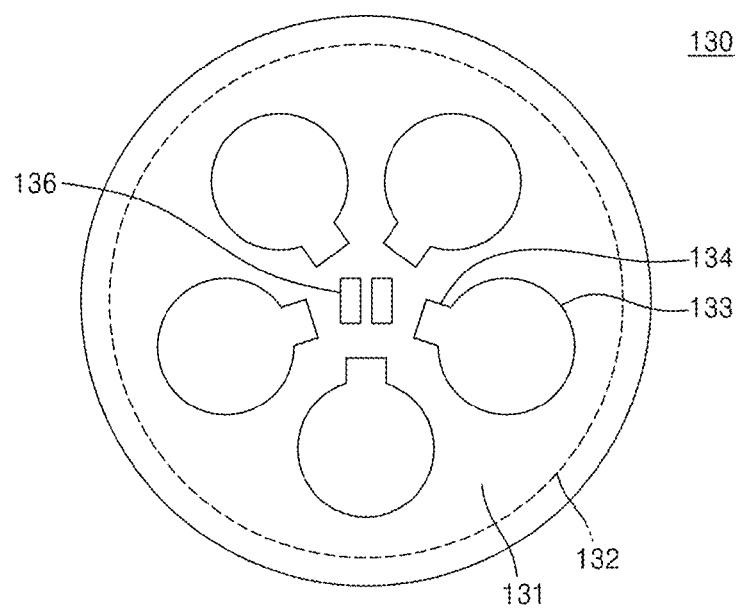
FIG. 7 is a plan view of a holder in FIG. 6.
Figure 8:
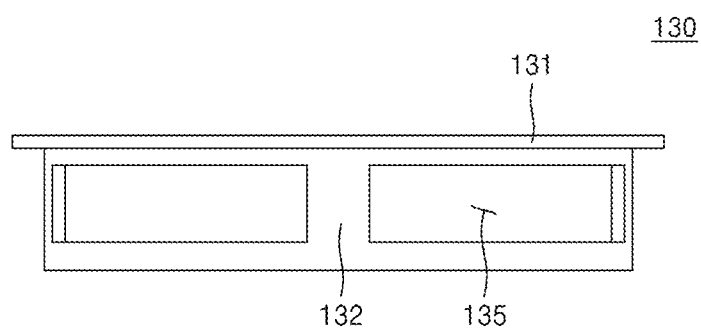
FIG. 8 is a front view of a holder in FIG. 6.

FIG. 6 is an exploded perspective view showing the culture unit 100 according to an embodiment of the present disclosure, FIG. 7 is a plan view of a holder 130 in FIG. 6, and FIG. 8 is a front view of the holder 130 in FIG. 6.

Referring to FIGS. 6 to 8, the culture unit 100 may provide the space for culturing the cell. In the present specification, the term of the culture unit 100 may be used interchangeably with names such as a culture apparatus, a culture dish, or the like.

The culture unit 100 may include a main body 110, a cover 120, the holder 130, a first insert 140 and/or a second insert 150. The first insert 140 and the second insert 150 may be selectively mounted in the holder 130 depending on a purpose of use or a function of the cell culture apparatus 1.

For example, as shown in FIG. 6, only the plurality of first inserts 140 may be mounted in the holder 130, or only the plurality of second inserts 150 may be mounted in the holder 130. In addition, the first insert 140 and/or the second insert 150 may be mounted only in a portion of insertion openings of the holder 130.

The main body 110 may have a connecting end 111 through which the culture medium is introduced or discharged, and may store the culture medium in an inner space defined therein. The holder 130 and the inserts are arranged inside the main body 110, and a top of the main body 110 may be covered by the cover 120.

A shape of the main body 110 may not be limited to a specific shape, and may be variously set, such as a polygonal shape, a circular shape, and the like. However, hereinafter, for convenience of description, an embodiment in which the main body 110 has the circular shape will be mainly described.

The holder 130 may be mounted inside the main body 110. A bottom of the main body 110 may support the holder 130. In addition, the connecting end 111 is installed on a side wall of the main body 110, so that the culture medium may be introduced and/or discharged.

In an embodiment, the two connecting ends 111 may be installed on the main body 110. One connecting end 111 may be connected to the conduit C, so that the culture medium may be introduced. Further, the other connecting end 111 may be connected to the conduit C, so that the culture medium may be discharged.

In another embodiment, the connecting end 111 may include at least three connecting ends. The plurality of conduits C may be connected to the at least three connecting ends to increase the flow rate of the culture medium, which is introduced or discharged, and introduce or discharge various types of culture media.

The cover 120 may be disposed to cover the top of the main body 110, and a gas supplier 121 may be defined in the cover 120. The gas supplier 121 is a passage through which air necessary for the culture may enter and exit. A filter (not shown) may be disposed inside the gas supplier 121. External air may pass through the gas supplier 121 and flow into the culture unit 100, and foreign matter is filtered by the filter.

In another embodiment, the external gas may be supplied through the gas supplier 121. For example, oxygen, carbon dioxide, nitrogen, or other gas required for the culture may be supplied into the culture unit 100 through a gas supply unit (not shown) mounted in the gas supplier 121. Specifically, when the animal cell is cultured in the culture unit 100, the oxygen may be supplied, and when the plant cell is cultured, the carbon dioxide may be supplied.

In an embodiment, the cover 120 may be detachably assembled to the main body 110. Spiral protrusions of the cover 120 and the main body 110 may be engaged with each other, so that the cover 120 and the main body 110 may be assembled with each other. In another embodiment, the cover and the body may be formed in one body.

The holder 130 may be disposed in the inner space of the main body 110 and may have a plurality of insertion openings 133. At least one insert is inserted into the holder 130, so that the culture module 10 may stably support the insert during the agitation. The holder 130 may include a support plate 131, a side wall 132, an insertion opening 133, a guide opening 134, a side opening 135, and a center hole 136.

At least one insertion opening 133 may be defined in the support plate 131. FIG. 6 shows that the holder 130 has the five insertion openings 133. However, the present disclosure may not be limited thereto, and may be variously set depending on a size and the purpose of the culture of the culture unit 100.

The support plate 131 is disposed to correspond to the shape of the main body 110, and is installed in the inner space of the main body 110. The support plate 131 supports the inserted insert, so that the culture unit 100 may stably hold the insert even when being shaken during the agitation.

The side wall 132 is disposed beneath the support plate 131 and is in contact with the bottom of the main body 110. The plurality of side openings 135 are defined in the side wall 132, so that the culture medium introduced into the connecting end 111 may be introduced into the inner space of the holder 130.

The insertion opening 133 may be defined in the support plate 131, the insert may be inserted into the insertion opening 133 and be supported. A shape of the insertion opening 133 may correspond to a shape of the insert.

The guide opening 134 is connected to one side of the insertion opening 133. The guide opening 134 provides a space for inserting or removing the insert. When the insert is inserted into the holder 130 or removed from the holder 130, the user grips the insert with a tool such as tweezers and the like. Because the guide opening 134 provides a space for an end of the tool such as the tweezers and the like to enter, the user may conveniently insert the insert into the insertion opening 133 of the holder 130 or remove the insert from the insertion opening 133 while gripping the insert. Specifically, an incision groove of the insert is disposed in the guide opening 134, thereby increasing a freedom of the user.

The side opening 135 is defined in the side wall 132, so that the culture medium may pass through the side opening 135. The plurality of side openings 135 may be defined, so that the culture medium may be introduced into the inner space of the holder 130.

Figure 13:
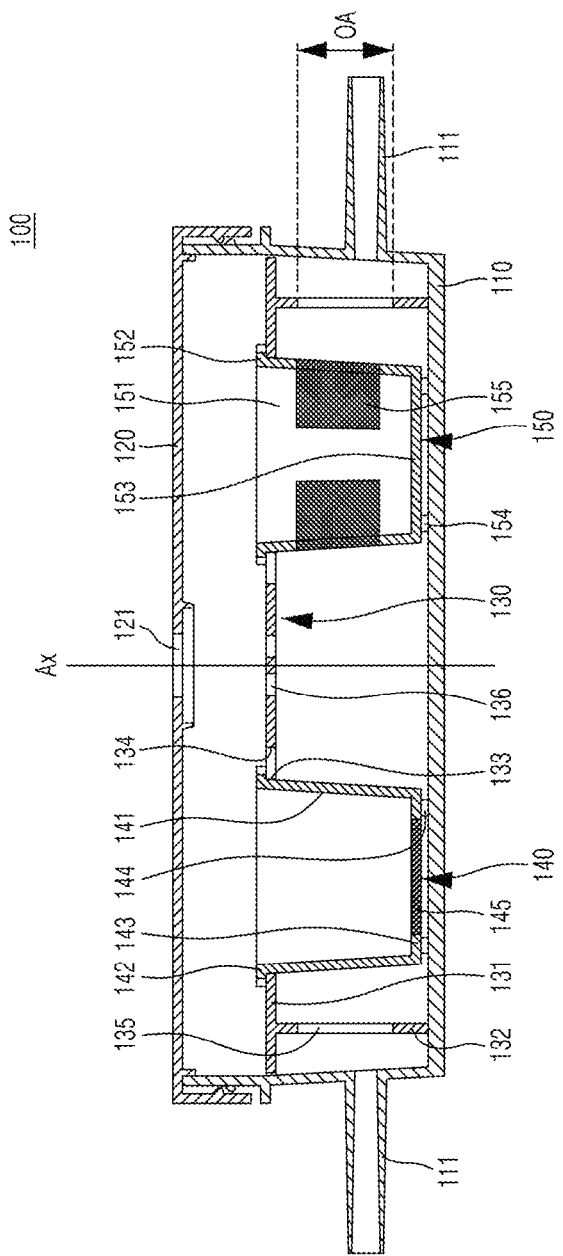
FIG. 13 is a cross-sectional view showing a cross-section of one embodiment of a culture unit in FIG. 6.

The side opening 135 may be defined to face the connecting end 111. Referring to FIG. 13, the side opening 135 has a predetermined opening area OA, and the connecting end 111 is disposed to face the side opening 135. As a result, the culture medium introduced into the connecting end 111 may pass through the side opening 135 and be rapidly introduced into the inner space of the holder 130. In addition, the culture medium to be discharged to the connecting end 111 may also rapidly pass through the side opening 135 and be discharged from the main body 110 to the conduit C.

The center hole 136 may be defined at a center of the holder 130, and may be used when the holder 130 is mounted in or separated from the main body 110. The user may grasp the holder 130 by inserting the tool such as the tweezers and the like into the center hole 136.

Figure 9:
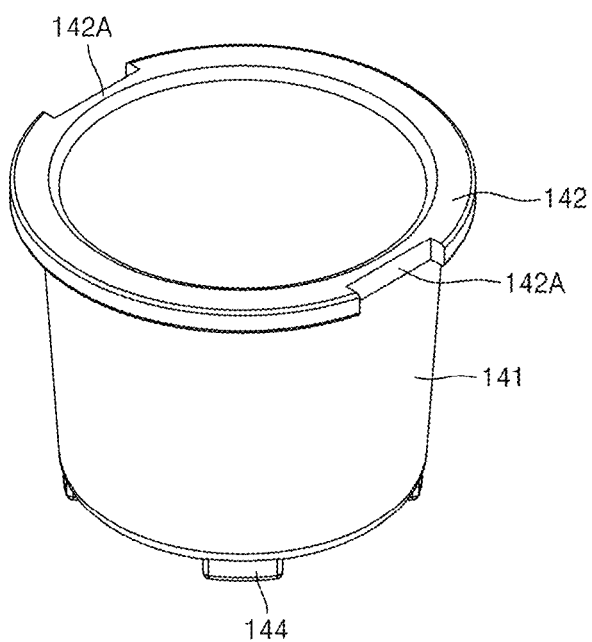
FIGS. 9 and 10 are perspective views showing an insert in FIG. 6.
Figure 10:
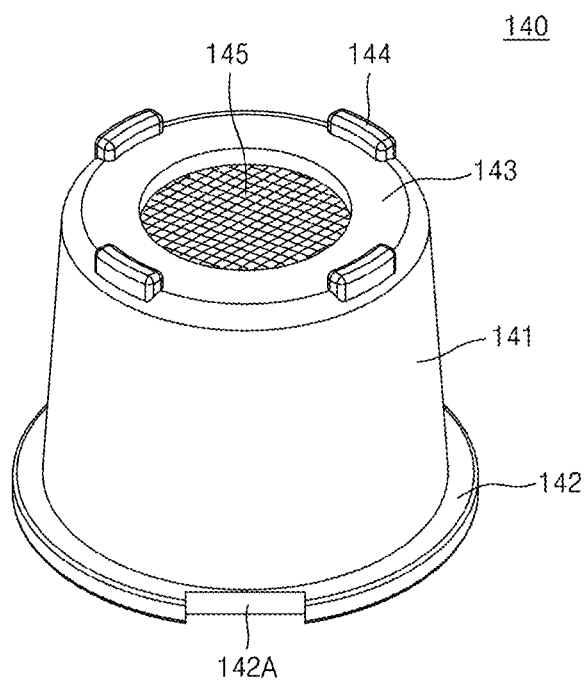

FIGS. 9 and 10 are perspective views showing an insert in FIG. 6.

Referring to FIGS. 9 and 10, the first insert 140 may include a first main body 141, a first tip 142, a first bottom 143, a first support protrusion 144, and a first fluid passing portion 145.

The first main body 141 is extended to have a predetermined length, and the first bottom 143 is disposed at a bottom of the first main body 141, so that the first main body 141 may have an inner space defined therein. The cell to be cultured may be installed in the inner space of the first main body 141.

The first tip 142 may be disposed at an upper end of the first main body 141, and may be slightly protruded in a radius direction. The first tip 142 is supported by the insertion opening 133, so that the first insert 140 may be supported by the holder 130.

A first incision groove 142A may be defined in the first tip 142. In an embodiment, the pair of first incision grooves 142A may be defined to face each other. The first incision groove 142A provides a space for the user to grip the first insert 140 with the tool. In particular, the first incision groove 142A is aligned with the guide opening 134 of the holder 130, so that the first insert 140 may be easily inserted into or removed from the holder 130.

The first support protrusion 144 may be disposed beneath the first bottom 143 and may be in contact with the bottom of the main body 110. Because an upper end of the first insert 140 is supported by the holder 130 by the first tip 142 and a lower end of the first insert 140 is supported by the main body 110 by the first support protrusion 144, the first insert 140 may maintain stability even when a strong agitation motion is applied to the culture module 10.

The first fluid passing portion 145 may be disposed on the first bottom 143. The first fluid passing portion 145 is a structure through which the culture medium may pass. For example, the first fluid passing portion 145 may have a mesh structure. In another embodiment, the first fluid passing portion 145 may have a membrane shape that selectively passes some material.

Because the first fluid passing portion 145 is disposed on the first bottom 143, the culture medium passes through the first fluid passing portion 145 while flowing downwards in the first insert 140. Therefore, a cell cultured in the first insert 140 may include a cell of an organ responsible for absorption, such as an intestinal cell.

Figure 11:
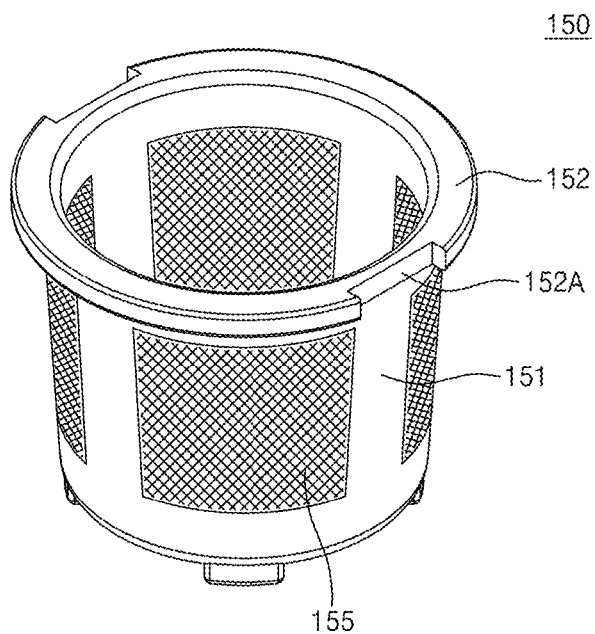
FIGS. 11 and 12 are perspective views showing another embodiment of an insert.
Figure 12:
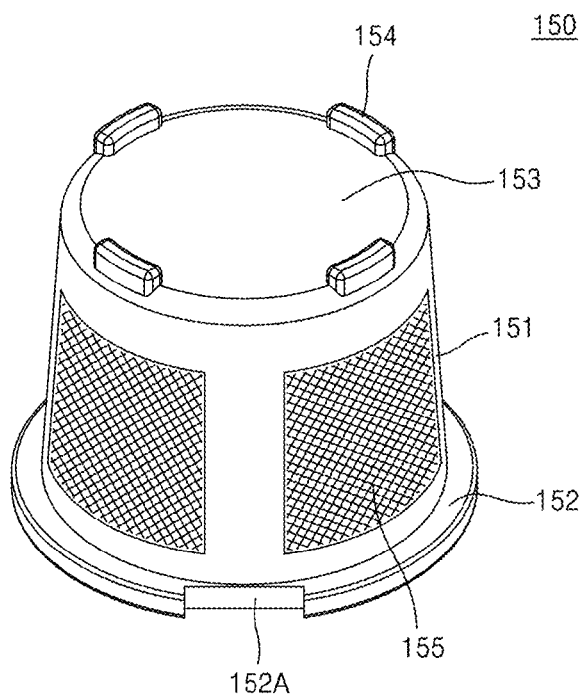

FIGS. 11 and 12 are perspective views showing another embodiment of an insert.

Referring to FIGS. 11 and 12, the second insert 150 may include a second main body 151, a second tip 152, a second bottom 153, a second support protrusion 154, and a second fluid passing portion 155. Compared to the first insert 140 described above, the second insert 150 has a technical feature in an arrangement of the second fluid passing portion 155. Thus, hereinafter, an overlapping description will be omitted or summarized, and differences will be mainly described.

The second fluid passing portion 155 may be disposed on the second main body 151. Because the second fluid passing portion 155 is disposed on a side surface of the second insert 150, the culture medium may flow in a lateral direction in the second insert 150. Therefore, a cell cultured in the second insert 150 may include a cell of an organ responsible for metabolism and toxicity, such as a liver cell or a kidney cell.

FIG. 13 is a cross-sectional view showing a cross-section of one embodiment of a culture unit in FIG. 6.

Referring to FIG. 13, the culture unit 100 may have the inner space defined therein as the cover 120 is mounted on the top of the main body 110, and the holder 130 may be installed in the inner space. The first insert 140 may be mounted in the holder 130 as shown in a left side of FIG. 13. In addition, the second insert 150 may be mounted in the holder 130 as shown in a right side of FIG. 13.

FIG. 13 illustrates that the first insert 140 and the second insert 150 are mounted in the holder 130 for convenience of description, but the present disclosure is not limited thereto. Only the first insert 140 may be mounted in the holder 130 as an example, or only the second insert 150 may be mounted in the holder 130 as another example.

Figure 14:
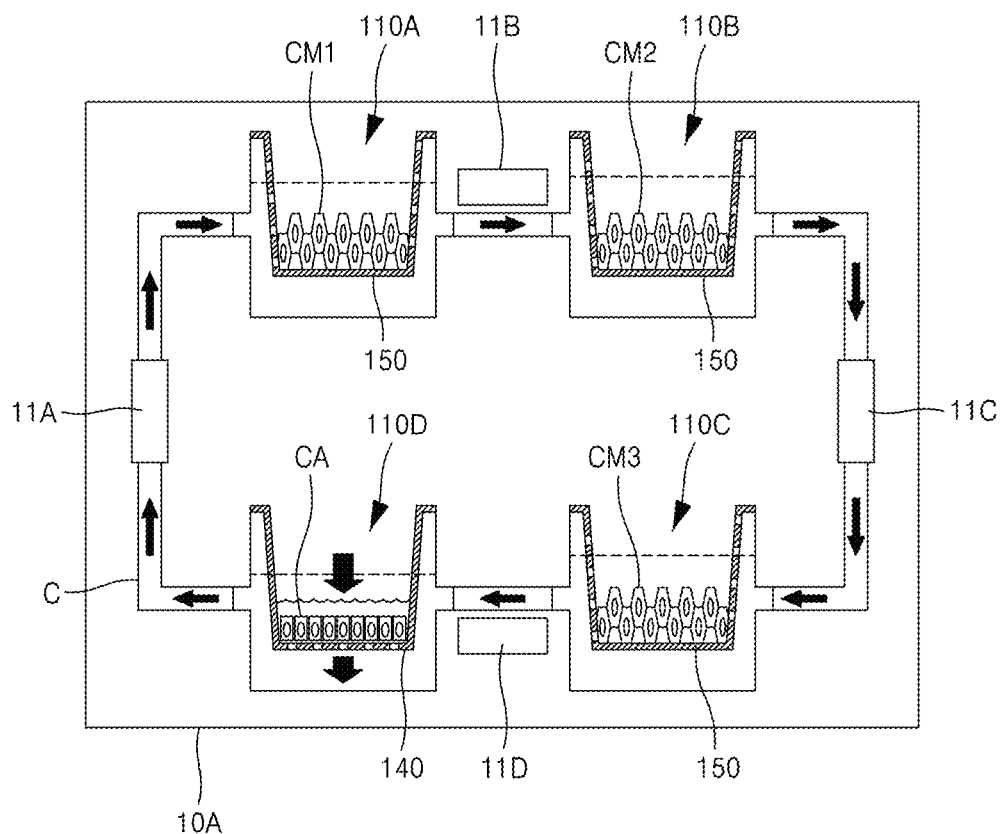
FIG. 14 is a view showing an embodiment of culturing a cell with a culture module according to an embodiment of the present disclosure.

FIG. 14 is a view showing an embodiment of culturing a cell with the culture module 10 according to an embodiment of the present disclosure.

Referring to FIG. 14, each cell may be cultured with each of the first to the fourth culture units 100A to 100D arranged in the culture module 10. The first to the fourth culture units 100A to 100D have a structure that circulates by the conduit, thereby implementing a culture apparatus that mimics the body.

The culture module 10 may culture the cells respectively in the first to the fourth culture units 100A to 100D based on a circulation order of blood. For example, when the blood flows in an order of a first organ, a second organ, a third organ, and a fourth organ in the body, the culture medium may circulate the blood in an order of the first culture unit 100A, the second culture unit 100B, the third culture unit 100C, and the fourth culture unit 100D. A first cell CM1, which is a cell of the first organ, is cultured in the first culture unit 100A, a second cell CM2, which is a cell of the second organ, is cultured in the second culture unit 100B, a third cell CM3, which is a cell of the third organ, is cultured in the third culture unit 100C, and a fourth cell CA, which is a cell of the fourth organ, is cultured in the fourth culture unit 100D.

Because the plurality of cells are cultured based on the circulation order of the blood, the cell culture apparatus 1 may evaluate a performance similar to the body. Because the culture medium introduced into or discharged from the culture units 100 reflects a result of interactions of the various types of cells, the culture medium is able to implement a situation very similar to the body while circulating through the culture units 100. For example, when each cell is cultured with culture medium containing a specific drug to measure a human response to the specific drug, drug efficacy result data reflecting interactions of the cells may be obtained.

The culture module 10 may include the insert placed in each culture unit 100, which is selected based on characteristics of the cell cultured in each culture unit 100.

For example, the first cell CM1 having a metabolic function is cultured in the first culture unit 100A, the second cell CM2 having the metabolic function is cultured in the second culture unit 100B, and the third cell CM3 having the metabolic function is cultured in the third culture unit 100C. The fourth cell CA having an absorption function may be cultured in the fourth culture unit 100D.

In this connection, the second insert 150 is placed in the first to the third culture units 100A to 100C to culture the first to the third cells CM1 to CM3 having the metabolic function. The first insert 140 may be placed in the fourth culture unit 100D to culture the fourth cell CA having the absorption function.

Because the insert placed in each culture unit 100 is set based on the characteristics of the cell to be cultured, the cell culture apparatus 1 may set flow of the culture medium based on the characteristics of the cell. When the cell of the organ responsible for the absorption is cultured, the first insert 140 having the fluid passing portion disposed at the bottom thereof may be placed in the culture unit 100, and the culture medium may flow downwards from a top of the first insert 140. In addition, when the cell of the organ responsible for the metabolism and the toxicity is cultured, the second insert 150 having the fluid passing portion disposed on the side surface thereof may be placed in the culture unit 100, and the culture medium may flow in a left and right direction of the second insert 150.

The cell culture apparatus 1 may set the number of inserts to be placed in each culture unit 100 based on a relative ratio of the cells to be cultured. That is, the cell culture apparatus 1 may set a size or the number of cells cultured in each culture unit 100 based on a relative ratio of each organ. Because the ratio of each organ occupied in the body is considered, the interactions of the cells are substantially reflected during the cell culture. Thus, when measuring the efficacy and the like of the drug using the cell culture apparatus 1, result data having a very high similarity to a result of the human body may be obtained.

For example, based on a ratio of the first organ and the second organ, the number or a volume ratio of the first cell CM1 and the second cell CM2 may be set. Based on the ratio, the number of second inserts 150 to be cultured in the first culture unit 100A and the second culture unit 100B may be set, respectively. In addition, a ratio of the third or the fourth organ is considered in the same manner. The number of second inserts 150 in which the third cells CM3 are cultured in the third culture unit 100C may be set, and the number of first inserts 140 in which the fourth cells CA are cultured in the fourth culture unit 100D may be set.

When the number of inserts of each culture unit 100 is set in the same manner as above, because the ratio that each organ of the cells to be cultured is occupying in the body is considered, the cells are cultured while interacting with each other in the culture module 10 similarly to the organs interacting with each other in the body. Therefore, the cell culture apparatus 1 may be set in the situation very similar to a human body, and the result data obtained using the cell culture apparatus 1 may have a very high similarity to the result of the human body.

Figure 15:
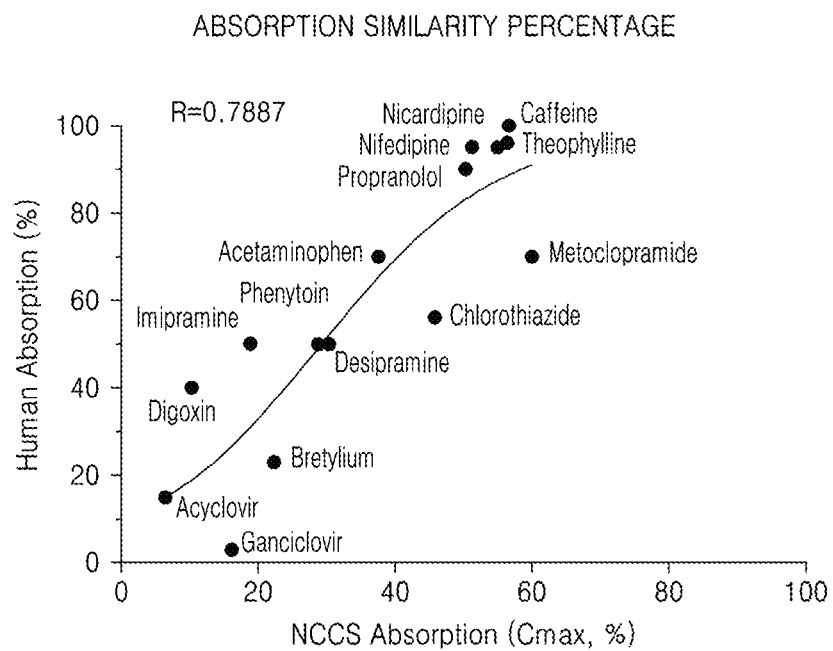
FIGS. 15 and 16 are graphs showing a similarity between an absorption degree and a metabolism degree measured using a cell culture apparatus according to the present disclosure.
Figure 16:
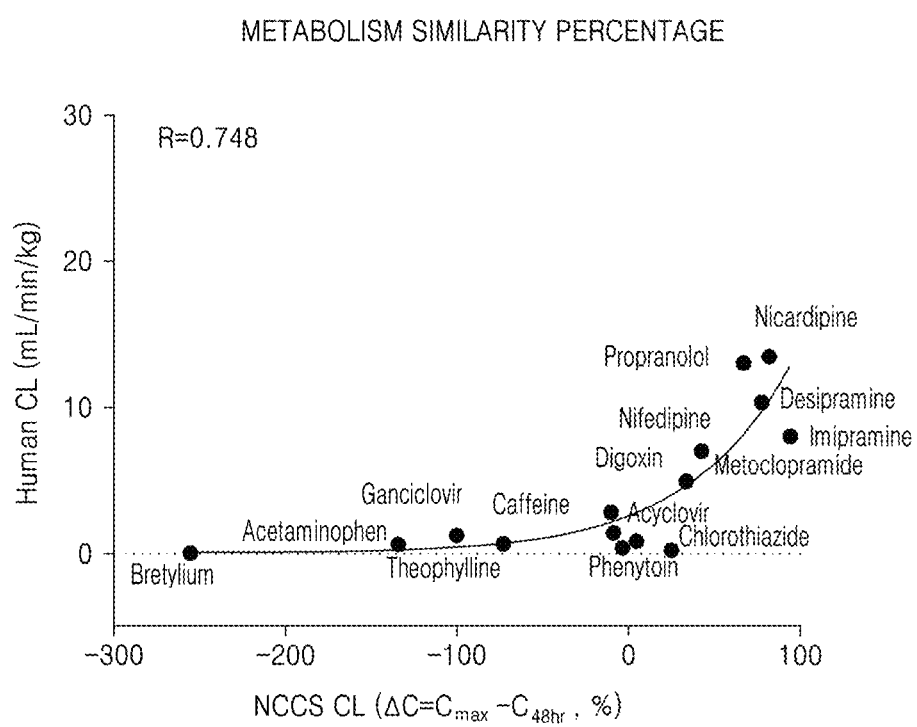

FIGS. 15 and 16 are graphs showing a similarity between an absorption degree and a metabolism degree measured using the cell culture apparatus 1 according to the present disclosure.

Referring to FIGS. 15 and 16, it may be seen that the cell culture apparatus 1 according to an embodiment of the present disclosure has the very high similarity to the result of the human body.

The intestinal cell responsible for the absorption and the liver cell responsible for the metabolism and the toxicity were mounted in the cell culture apparatus 1 and were subjected to circulated culture. A change in concentration of a drug by absorption and metabolism by time after an oral drug was put on the intestinal cell was measured, and the similarity was evaluated.

FIG. 15 shows a similarity of the concentration evaluation for the absorption of the drug. Compared to the result of the human body, the concentration evaluation for the absorption of the drug through the cell culture apparatus 1 has a high similarity of approximately 78.87%.

FIG. 16 shows a similarity of the concentration evaluation for the metabolism of the drug. Compared to the result of the human body, the concentration evaluation for the metabolism of the drug through the cell culture apparatus 1 has a high similarity of approximately 74.8%.

Figure 17:
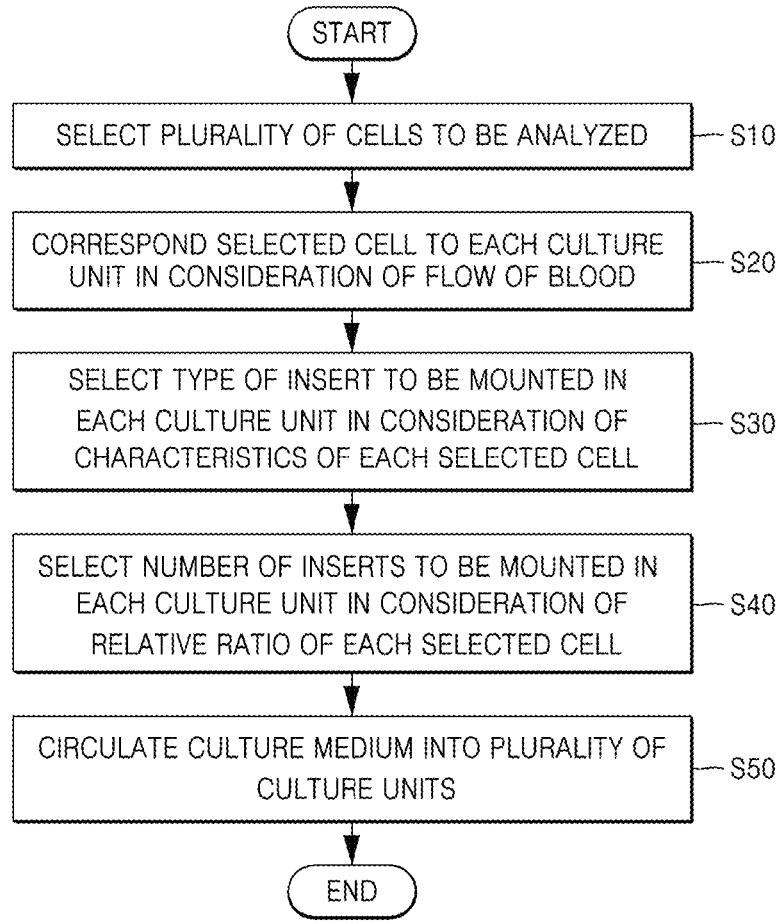
FIG. 17 is a flowchart illustrating a cell culture method according to another embodiment of the present disclosure.

FIG. 17 is a flowchart illustrating a cell culture method according to another embodiment of the present disclosure.

Referring to FIG. 17, a cell culture method may include selecting a plurality of cells to be analyzed (S10), corresponding the selected cell to each culture unit based on a flow of blood (S20), selecting a type of an insert to be placed in each culture unit based on characteristics of each selected cell (S30), selecting the number of inserts to be placed in each culture unit based on a relative ratio of each selected cell (S40), and circulating culture medium into the plurality of culture units (S50).

The selecting of the plurality of cells to be analyzed (S10) includes selecting different types of cells to be cultured using the cell culture method.

The corresponding of the selected cell to each culture unit based on the flow of the blood (S20) includes determining an order of the selected cells based on the flow of the blood circulating through organs.

The order of the cells cultured in the culture units is selected to correspond to the order of the organs based on the flow of the blood. Because the culture order of the cells is determined based on the flow of the blood, the cell culture method may increase a similarity to a body.

The selecting of the type of the insert to be place in each culture unit based on the characteristics of each selected cell (S30) may include setting the type of the insert to be placed in each culture unit based on each characteristics of the cell to be cultured. Because each selected insert may reflect the characteristics of the cell to be cultured inside to form a flow of the culture medium, the cell culture method may culture each cell while the characteristics of each cell are optimized.

The selecting of the number of inserts to be placed in each culture unit based on the relative ratio of each selected cell (S40) may include setting a size or the number of cells based on a relative ratio of each organ in the body.

For example, when a cell to be cultured in a first culture unit is a liver cell and a cell to be cultured in a second culture unit is a kidney cell, the number of inserts to be placed in the first culture unit and the number of inserts to be placed in the second culture unit may be set based on a relative ratio of a liver and a kidney. The cells interact with each other in a state in which an actual ratio of each organ in the body is reflected, so that the cultured cells may have very a high similarity to a human body.

The circulating of the culture medium into the plurality of culture units (S50) may include supplying the culture medium to the culture unit based on the flow of the blood. Because the culture media introduced into or discharged from the culture units interact with each other, the similarity to the body may be increased.

In this connection, the cell culture method may agitate the culture unit to facilitate contact of a substance in the culture medium with the cell, thereby promoting introduction of the substance into the cell.

In addition, in the cell culture method, to test an effect of a drug, the corresponding drug may be injected into each culture unit. For example, a metabolism of the corresponding drug may be measured by injecting the corresponding drug into the first culture unit in which the liver cell is cultured.

Because the cell culture method according to an embodiment of the present disclosure cultures the cell based on the characteristics of each cell to be cultured, the culture result with the high similarity to the body may be achieved. Because the order of the cells to be cultured is determined based on the flow of the blood, the cell culture method has the very high similarity to the result of the human body. In addition, because the cell culture method selects the insert based on the characteristics of the cell, the cell may be cultured to be suitable for the characteristics of each cell, and result data thereof may be obtained. In addition, the cell culture method considers the relative ratios of the cells of the plurality of types to be cultured, so that the cells cultured may have the substantial similarity to the human body.

As such, the present disclosure has been described with reference to the embodiment shown in the drawings, but this is only exemplary. Those skilled in the art will understand that various modifications and other equivalent embodiments are possible therefrom. Therefore, the true technical protection scope of the present disclosure should be determined by the technical spirit of the appended claims.

In the cell culture apparatus and the cell culture method according to an embodiment of the present disclosure, the culture units in which the cells are cultured are connected to each other during the culture, so that the interactions between the cells are implemented. Thus, a change in the drug or the extracellular substance may be tested.

In the cell culture apparatus and the cell culture method according to an embodiment of the present disclosure, as the cell unit in which the cell is cultured is agitated during the culture, the contact between the cell and the substance (e.g., the drug, a growth factor, and the like) in the culture medium is facilitated. Thus, an input efficiency in the cell may be increased, so that a change in the cell culture by the substance may be effectively tested.

In the cell culture apparatus and the cell culture method according to an embodiment of the present disclosure, the flow of the culture medium may be set based on unique characteristics of the cell to be cultured. The flow direction of the culture medium may be adjusted by selecting the type of the insert do be disposed in the culture unit with consideration of the characteristics of the cell.

In the cell culture apparatus and the cell culture method according to an embodiment of the present disclosure, the number of inserts to be placed in each culture unit may be set based on the relative ratios of the cells to be cultured. Because, the ratio occupied by each organ in the body is considered, the interactions between the cells are substantially reflected during the cell culture, so that accurate result data may be obtained. The scope of the present disclosure is not limited by such effects.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A cell culture apparatus comprising:
a plurality of culture units configured to culture cells;
a conduit configured to connect the plurality of culture units to each other to form a circulating path;
a pump unit on the conduit and configured to form a flow in culture medium such that the culture medium circulates through the plurality of culture units; and
an agitating module including a driver and configured to agitate the plurality of culture units,
wherein each of the culture units includes,
a main body connected to the conduit,
a holder in an inner space of the main body and having a plurality of insertion openings defined therein, and
an insert configured to be inserted into at least one of the insertion openings and supported by the holder, the insert further configured to arrange cells therein,
wherein the insert includes a fluid passing portion on at least one of a bottom or a side wall of the insert, and
wherein the fluid passing portion is configured to pass the culture medium therethrough.

2. The cell culture apparatus of claim 1, wherein the agitating module is configured to move or shake the plurality of culture units in at least one direction.

3. The cell culture apparatus of claim 1, further comprising:
a stage having one surface for mounting the plurality of culture units thereon and another surface connected to the agitating module.

4. The cell culture apparatus of claim 1, wherein the holder further includes at least one side opening defined in a side wall thereof and configured to face the conduit.

5. The cell culture apparatus of claim 1, wherein the holder further includes a guide opening connected to one side of each of the insertion openings.

6. The cell culture apparatus of claim 1, wherein the fluid passing portion has a mesh shape.

7. The cell culture apparatus of claim 1, wherein a number of inserts to be placed in each of the culture units is set based on a relative ratio of each cell to be cultured in the each of the culture units.

8. The cell culture apparatus of claim 1, further comprising:
a load cell unit below each of the culture units and configured to measure an amount of culture medium introduced into the each of the culture units.

9. The cell culture apparatus of claim 8, further comprising:
a controller configured to drive the pump unit to adjust the culture medium stored in each of the culture units based on weight data of the each of the culture units measured by the load cell unit.

10. The cell culture apparatus of claim 1, further comprising:
a sub-unit connected to a circulation circuit connected to the conduit, wherein the sub-unit is configured to supply or extract fluid to or from the conduit.

11. A cell culture apparatus comprising:
a main body having a connecting end and configured to store culture medium therein, the main body is configured to introduce the culture medium into the connecting end;
a holder in an inner space of the main body and having a plurality of insertion openings; and
an insert configured to be inserted into at least one of the insertion openings and supported by the holder, the insert further configured to arrange cells therein,
wherein the holder further includes a guide opening connected to one side of each of the insertion openings.

12. The cell culture apparatus of claim 11, wherein the holder further includes at least one side opening defined in a side wall thereof to face the connecting end.

13. The cell culture apparatus of claim 11, wherein the insert includes a fluid passing portion on at least one of a bottom or a side wall of the insert, and the fluid passing portion is configured to pass the culture medium therethrough.

14. A cell culture system comprising:
a plurality of cell culture apparatuses interconnected with each other so that culture medium circulates,
wherein each of the plurality of cell culture apparatuses includes,
a main body having a connecting end and configured to store the culture medium therein, the main body is configured to introduce the culture medium into the connecting end,
a holder in an inner space of the main body and having a plurality of insertion openings; and
an insert configured to be inserted into at least one of the insertion openings and supported by the holder, the insert further configured to arrange cells therein,
wherein a number of inserts to be placed in each cell culture apparatus is set based on a relative ratio of each cell to be cultured, and
wherein the insert includes a fluid passing portion on at least one of a bottom or a side wall of the insert, the fluid passing portion configured to pass the culture medium therethrough.

* * * * *